(12) United States Patent
Butler et al.

(10) Patent No.: US 9,089,651 B2
(45) Date of Patent: Jul. 28, 2015

(54) DOSE SETTING MECHANISM

(75) Inventors: Joseph Butler, Warwickshire (GB); David Plumptre, Wrocestershire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 13/878,464

(22) PCT Filed: Oct. 11, 2011

(86) PCT No.: PCT/EP2011/067680
§ 371 (c)(1),
(2), (4) Date: Apr. 9, 2013

(87) PCT Pub. No.: WO2012/049143
PCT Pub. Date: Apr. 19, 2012

(65) Prior Publication Data
US 2013/0197448 A1 Aug. 1, 2013

Related U.S. Application Data

(60) Provisional application No. 61/392,756, filed on Oct. 13, 2010.

(30) Foreign Application Priority Data

May 31, 2011 (EP) ..................................... 11168193

(51) Int. Cl.
*A61M 5/315* (2006.01)

(52) U.S. Cl.
CPC ......... *A61M 5/31536* (2013.01); *A61M 5/3158* (2013.01); *A61M 5/31525* (2013.01); *A61M5/31551* (2013.01); *A61M 5/31571* (2013.01); *A61M 5/31593* (2013.01); *A61M 5/31535* (2013.01); *A61M 5/31541* (2013.01)

(58) Field of Classification Search
CPC ..................... A61M 5/31551; A61M 5/31535; A61M 5/31525; A61M 5/31593; A61M 5/31541; A61M 5/3155; A61M 5/31528; A61M 5/31533
USPC ......... 604/207–211, 218–222, 150–157, 238, 604/66, 122
See application file for complete search history.

(56) References Cited

U.S. PATENT DOCUMENTS 5,674,204 A * 10/1997 Chanoch ....................... 604/211
2008/0077094 A1 3/2008 Burren et al.
(Continued)

FOREIGN PATENT DOCUMENTS

CN 1780652 5/2006
CN 101124005 2/2008
(Continued)

OTHER PUBLICATIONS

International Search Report and Written Opinion for Int. App. No. PCT/EP2011/067680, completed Jan. 24, 2012.
(Continued)

*Primary Examiner* — Nicholas Lucchesi
*Assistant Examiner* — Weng Lee
(74) *Attorney, Agent, or Firm* — McDonnell Boehnen Hulbert & Berghoff LLP

(57) ABSTRACT

A system for preventing delivery of less than a predetermined minimum dose of a medicament by providing a dose setting mechanism having a clutch ring rotationally fixed relative to the housing when a dose less than the minimum allowable dose is selected. The dose setting mechanism also includes a drug delivery device housing and a dose dial component positioned in the housing and rotatable during a dose setting step. A drive sleeve is positioned within the dose dial component, a spindle is positioned within the drive sleeve, and a clutch is positioned between the dose dial component and the drive sleeve. When the dose dial component is rotated to select a dose less than a minimum dose, a clutch ring prevents the drive sleeve from rotating to thereby prevent the selected dose from being administered.

15 Claims, 5 Drawing Sheets

(56) References Cited

U.S. PATENT DOCUMENTS

2008/0208142 A1* 8/2008 Moller .......................... 604/208
2009/0275916 A1* 11/2009 Harms et al. .................. 604/506
2014/0316349 A1  10/2014 Veasey et al.

FOREIGN PATENT DOCUMENTS

| EP | 1074273 | 2/2001 |
|----|---------|--------|
| WO | 2004/028598 | 4/2004 |
| WO | 2004/078239 | 9/2004 |
| WO | 2006/089768 | 8/2006 |
| WO | 2009/105910 | 9/2009 |
| WO | 2010/139691 | 12/2010 |

OTHER PUBLICATIONS

International Preliminary Report on Patentability for Int. App. No. PCT/EP2011/067680, mailed Apr. 25, 2013.
Chinese Office Action for CN App. No. 2011800598805.8, dated Oct. 24, 2014.

* cited by examiner

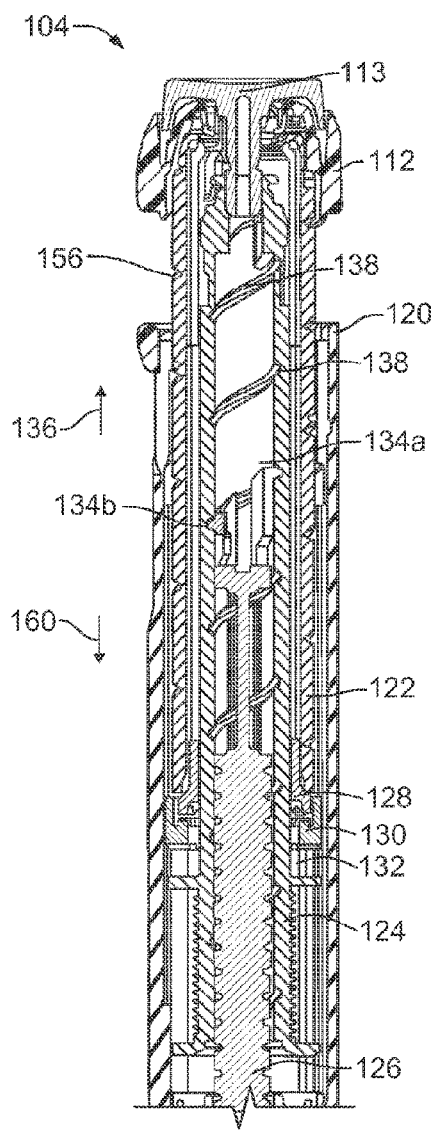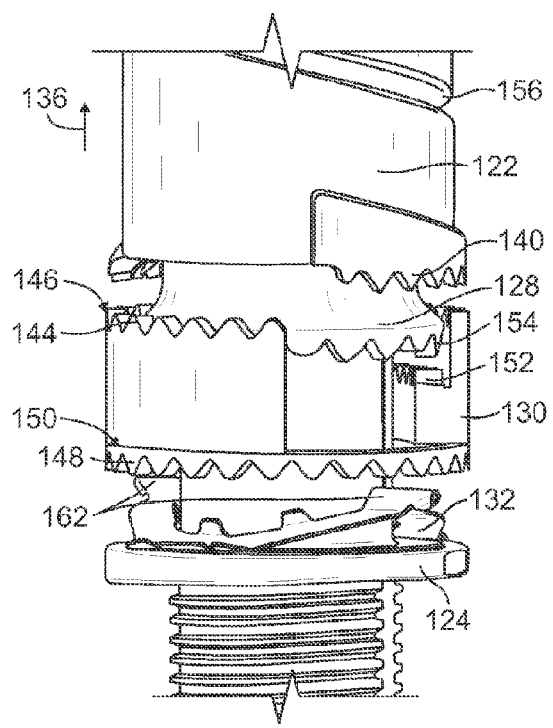
FIG. 1B
FIG. 2A

DOSE SETTING MECHANISM

CROSS REFERENCE TO RELATED APPLICATIONS

The present application is a U.S. National Phase Application pursuant to 35 U.S.C. §371 of International Application No. PCT/EP2011/067680 filed Oct. 10, 2011, which claims priority to U.S. Provisional Patent Application No. 61/392,756 filed Oct. 13, 2010 and European Provisional Patent Application No. 11168193.8 filed May 31, 2011. The entire disclosure contents of these applications are herewith incorporated by reference into the present application.

BACKGROUND

The present patent application is generally directed to dose setting mechanisms for drug delivery devices that control minimum and/or maximum possible dose settings. More particularly, the present patent application is generally directed to drug delivery devices, such as pen type drug delivery devices where therapy demands that a patient receive at least a certain minimum dose and not exceed a certain maximum dose of a particular medicament. Such devices provide for self-administration of medicinal product from a multi-dose cartridge and contain dose limiting mechanisms for setting minimum and/or maximum doses. The present application may find application in both disposable and reusable type drug delivery devices. However, aspects of the invention may be equally applicable in other scenarios as well.

Self administered injectable medicaments are often delivered using a variable-dose injection device. Such a device is known from WO 2004/078239 A1. Prior to the injection the user selects the dose that they require according to their prescribed dose and/or their current or expected future physical condition. A typical example would be an insulin delivery device for diabetics where a patient's dose is determined according to their prescribed dose and their expected food intake and activity level. Typically such devices allow the user to select any dose from 1 unit up to the maximum units that the device can deliver, typically 60 units or 80 units for a manual device, such as a pen-type or syringe injection device.

The drug delivery device of WO 2004/078239 A1 comprises a housing for receiving a dose setting mechanism, a cartridge, a dose dial sleeve with an attached dose dial grip, a clicker, a drive sleeve, a clutch for coupling and decoupling the dose dial sleeve and the drive sleeve, a rotatable piston rod and a button which is pressed for injecting a set dose. The full description of the pen-type injection devices disclosed in WO 2004/078239 A1 is incorporated herein by reference.

To dial a dose a user rotates the dose dial grip. With the clicker and clutch means engaged, the drive sleeve, the clicker, the clutch means and the dose dial sleeve rotate with the dose dial grip relative to the housing and relative to the piston rod. Audible and tactile feedback of the dose being dialed is provided by the clicker and the clutch means. Torque is transmitted through saw teeth between the clicker and the clutch means.

A helical groove on the dose dial sleeve and a helical groove in the drive sleeve have the same lead. This allows the dose dial sleeve to extend from the housing and the drive sleeve to climb the piston rod at the same rate. At the limit of travel, a radial stop on the dose dial sleeve engages a stop provided on the housing to prevent further movement. Rotation of the piston rod is prevented due to the opposing directions of overhauled and driven threads on the piston rod.

Should a user inadvertently dial beyond the desired dosage, the pen-type injector allows the dosage to be dialed down without dispense of medicinal product from the cartridge. The dose dial grip is counter rotated. This causes the system to act in reverse. The torque transmitted through the clutch means causes the saw teeth to ride over one another to create the clicks corresponding to dialed dose reduction. Preferably the saw teeth are so disposed that the circumferential extent of each saw tooth corresponds to a unit dose.

When the desired dose has been dialed, the user may then dispense this dose by depressing the button. This displaces the clutch means axially with respect to the dose dial sleeve causing dog teeth of the clutch means to disengage. However the clutch means remains keyed in rotation to the drive sleeve. The dose dial sleeve and associated dose dial grip are now free to rotate. The axial movement deforms a flexible part of the clicker to ensure the saw teeth cannot be overhauled during dispense. This prevents the drive sleeve from rotating with respect to the housing though it is still free to move axially with respect thereto. This deformation is subsequently used to urge the clicker and the clutch back along the drive sleeve to restore the connection between the clutch and the dose dial sleeve when pressure is removed from the button. The longitudinal axial movement of the drive sleeve causes the threaded piston rod to rotate through a threaded opening in a housing insert, thereby to advance the piston in the cartridge.

In other words, the drive sleeve moves longitudinally, i.e. only in the axial direction, during an injection. Because the drive sleeve and the piston rod are engaged via corresponding threads on the outer surface of the piston rod and an internal face of the drive sleeve, the longitudinal movement of the drive sleeve causes the piston rod to rotate. The housing insert with the threaded opening which is engaged with the piston rod via corresponding threads is fixed within the housing, i.e. prevented from rotation. Thus, the rotating piston rod is screwed through the threaded opening in the housing insert, i.e. the piston rod performs a combined rotational and longitudinal movement along a helical path defined by the corresponding threads of the threaded opening and the piston rod.

Once the dialed dose has been dispensed, the dose dial sleeve is prevented from further rotation by contact of a plurality of members extending from the dose dial grip with a corresponding plurality of stops formed in the housing, thus determining a zero dose position.

Such pen type drug delivery devices have been designed and developed to perform regular injections by persons without formal medical training. This is increasingly common among patients having diabetes where self-treatment enables such patients to conduct effective management of their disease. Because the patient, and not the health care worker, may be using such a drug delivery device, one requirement is that the device should be robust in construction. The drug delivery device must also be easy to use both in terms of the drug delivery device manipulation and understanding of the device's operation. This is especially true for diabetics who are required to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

In addition to insulin, other medicaments require a minimum dose to be delivered before they are therapeutically effective. A variable-dose device that allows the patient to deliver doses below the therapeutically effective minimum dose creates the possibility that the user may deliver the ineffective doses either by an error of dose calculation or by mistakenly selecting the incorrect dose. Likewise, some medicaments require that a maximum dose is not to be exceeded. This may be for safety reasons such as increased risk or severity of side-effects or excessive or unwanted actions of the medicament. Current variable-dose delivery devices typically have a maximum dose that is limited by the maximum dose that the delivery mechanism can provide, however, this does not necessarily relate to the maximum advised or prescribed dose of the medicament.

SUMMARY

The present invention has at least two applications. First, is the delivery of a single active medicament which must be a variable dose within a defined dose window, i.e. the dose must be more than a certain minimum dose and must not exceed a certain maximum dose. The second application relates to the delivery of a combined formulation of active medicaments where at least one of the medicaments is preferably delivered as a variable dose and at least one other medicament is preferably delivered as a fixed dose, and where this fixed dose can safely be allowed to vary within a defined dose window, for example by ±10% of the nominal fixed dose.

The minimum and/or maximum dose limited delivery device in accordance with the present invention could be used for a medicament that requires a minimum dose to be delivered before it becomes therapeutically effective, but where a degree of dose adjustment may be required. This dose adjustment may be required for a number of reasons, including tailoring a dose to a patient's body weight or the severity of their medical condition. The minimum and maximum dose limited device (min/max device) may also be used instead of a fully variable (i.e., 0 to max dose) device in order to reduce the possibility for dosing errors by the patient. Using the min/max device rather than a variable dose pen reduces the risk that a patient might accidentally deliver a dose outside the defined dose window, i.e., either too high or too low.

One example of the utility of the min/max device is where a parent could give the min/max delivery device to a child for the child to self-administer and the parent would know that the minimum and maximum levels of the min/max device limited the possible severity of any overdose or under dose. Another example of where such a device might be applicable is for patients who take long acting insulin. Typically a variable dose pen is required when a patient is "titrating" their dose to reach their target blood glucose level. However, once the target blood glucose level has been achieved the dose of long acting insulin typically remains more or less constant over relatively long periods of time. During this period, where their insulin dose is either constant or changes by only a few units on a day-to-day basis, the patient's long acting insulin needs could be effectively met by the minimum and maximum dose limited delivery device.

Table 1 (provided below) shows an example family of delivery devices, "Pen 1" through "Pen 4", which could be used in place of a single 1-80 unit variable dose device. Each of the Pens 1-4 are designed and manufactured around the same basic mechanism, but each pen contains either additional or alternative components which are used to set a different minimum and maximum dose. Patients would be prescribed a particular Pen according to their stable long acting insulin dose. For example, according to Table 1 a patient prescribed 30 units per day of long acting insulin would be prescribed Pen 2, which has a minimum dose of 18 units and a maximum dose of 42 units, respectively. Any number of mechanical components can be used in such a pen design to ensure these predetermined min/max doses, including axial and/or rotational stops, detents, clutches, compressible fingers, or the like components.

The insulin dose of diabetic patients may change gradually over time. Therefore there may be a small amount of dose range overlap between Pens to allow for a smooth transition between Pens as the dose increases. For example, according to Table 1 a patient prescribed 40 units per day of long acting insulin would be given Pen 2 if they expected their dose to decrease over time or Pen 3 if they expected their dose to increase over time. The number of pens in the "family" and the selected dose ranges shown in Table 1 are illustrative only. By using the min/max device of the present invention a mistake when selecting the dose is limited to within the pen's operating window. Dialing a dose above or delivering a dose below the pen's dose range would not be possible and this would alert the patient to their error.

The min/max device may also be applicable for the delivery of other medicines, particularly where there is a risk of confusion with similar devices that may lead to dose errors or drug/device mix-ups. One such example would be rapid acting insulin and long acting insulin. Both of these insulins are measured in "units" however the same number of units of each insulin type will have a very different effect and a patient will be prescribed different doses of each drug to be taken at different times throughout the day. A mix up of long acting and rapid acting insulin can cause hypoglycemia and is potentially fatal. Both types of insulin may be delivered by injection pen devices. Patients perform their injections on such a routine basis that an "automatic pilot" effect can occur where patients have been known to mix up their insulin pens, even though the pens are of different design, color, shape and carry different labels.

The presently proposed min/max device may help to prevent this mix up occurring. For example, assume both rapid acting and long acting insulins were each provided with a family of min/max devices according to Table 1. A patient is prescribed 50 units per day of long acting insulin (which would require long acting Pen 3) and 15 units of rapid acting insulin with meals (which would require Pen 1). The most dangerous mix up would occur if the patient mistakenly delivered 50 units of rapid acting insulin rather than long acting insulin. If the patient attempted to do this with the min/max devices then the patient would pick up the rapid insulin device (Pen 1) and find that they could not dial beyond 22 units. This should alert them to the fact that this is not the correct insulin pen, and therefore the incorrect insulin type, and prevent the incorrect insulin being delivered.

The min/max concepts may be applied equally to both disposable devices and reusable devices.

Certain medicines also require the user to perform a "priming" dose to confirm the correct operation of the delivery device and needle. This is usually accomplished by delivering an "air-shot" of 2 units and then checking that the medicine can be seen coming out of the needle. The min/max concept shown in Table 1 would not permit this. If priming functionality is required a second permissible "dose window", for example ranging from 1-2 units, may also be implemented within each pen mechanism. An example of how this could be applied is shown in Table 2. Although both Tables 1 and 2 show only even numbers of units this is done only for clarity and the device may be configured to deliver odd and even units or potential ½ units.

As mentioned, the presently disclosed devices may also be useful in therapies where the delivery of a combined formulation of active medicaments is needed, where at least one of the medicaments is preferably delivered as a variable dose and at least one other medicament is preferably delivered as a fixed dose. If a patient requires a combination of medicines then there is an advantage if those medicines can be provided as a single formulation (i.e. both drugs are mixed together in predefined proportions and supplied in one primary pack) for delivery by a single injection device in one injection through a single needle. However, if one of the drugs requires the delivery of a user-selectable variable dose and the second drug requires a dose above a minimum dose to be therapeutically effective and must not exceed a given maximum dose, then it is beneficial for the drug delivery device to be configured such that it is prevented from delivering doses that are outside of this range.

For example, a patient may be prescribed a combination therapy of long acting insulin (typically delivered in variable dose devices) and GLP-1 (typically delivered as a fixed dose). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of intensive investigation as a potential treatment of diabetes mellitus. In order to avoid the patient having to perform two injections the two medicines are pre-mixed into a single formulation. Since both medicaments are pre-mixed in a fixed ratio it is not possible to vary the long acting insulin dose without also varying the GLP-1 dose. However, it may be acceptable for the GLP-1 dose to vary within a given tolerance, for example ±10%, around a fixed nominal dose. It is therefore possible, using a family of min/max limited devices to provide a family of pre-mix devices which between them will allow delivery of a variable long acting insulin dose and a GLP-1 dose that always falls within ±10% of a given "fixed" dose.

Table 3, for example, shows a family of 6 min/max pen-type injection devices that allow the delivery of any long acting insulin dose from 22-76 units along with a GLP-1 dose that is "fixed" to 20 mg±10%. Each Pen within the family would have different minimum and maximum dose thresholds and would be provided with a primary pack or cartridge of medicament filled with the appropriate mix ratio of the two medicines. The family of pen devices could be provided as disposable mechanical devices, prefilled with the appropriate mix ratio cartridge of medicament. Alternatively, the family of devices could be provided as reusable mechanical devices. In the latter case, the devices would be preferably dedicated to a particular mix ratio cartridge, i.e. only the correct mix ratio cartridge can be loaded into each pen family member.

A third alternative is to provide the "family" of pen devices via a single electronic device that can be programmed with the minimum and maximum dose functionality. Preferably, the min/max electronic device would be loaded with a coded cartridge that would automatically upon being loaded into the device communicate to the device what the required minimum and maximum thresholds should be for that particular cartridge and mix ratio.

One specific means of achieving a minimum settable dose on a variable dose, drug delivery device, such as a pen-type device, is to include a mechanism that prevents dosing of the device until a predetermined minimum dose has been reached. A maximum dose mechanism can also be used with a minimum dose mechanism.

It is an object of the invention to provide a device that reduces or eliminates the risk that a user of an injection device will set and administer a dose below a preselected minimum effective dose of a particular medicament.

This object is solved with a dose setting mechanism as defined in claim 1.

According to one possible exemplary embodiment of the present invention a dose setting mechanism for a drug delivery device is provided comprising a minimum dose limiting function by means of a clutch ring that is rotationally fixed relative to a housing when a dose less than a minimum allowable dose is selected, but not when a dose greater than the minimum allowable dose is selected. In particular, the dose setting mechanism includes a drug delivery device housing and a dose dial component positioned in the housing and rotatable during a dose setting step. The dose setting mechanism may also include a drive sleeve positioned within the dose dial component and a spindle positioned within the drive sleeve. A clutch can be positioned between the dose dial component and the drive sleeve. As mentioned above, a clutch ring is rotationally fixed relative to the housing when a dose less than the minimum allowable dose is selected. When the dose dial component is rotated to select a dose less than a minimum dose, the clutch ring prevents the drive sleeve from rotating while the spindle disengages from the drive sleeve, thereby preventing the selected dose from being administered.

In known examples of pen-type devices that can incorporate the present invention, e.g. the device described in WO 2004/078239, the drive sleeve rotates together with the number sleeve during dose setting, while the drive sleeve is pushed axially without being able to rotate during dose administration. During dose setting and during dose administration, the drive sleeve is coupled to the spindle via engaging threads on the outer surface of the spindle and on the inner surface of the drive sleeve, respectively. In other words, one of the main principles of the present invention is to prevent (by means of the clutch ring) rotation of the drive sleeve during dose setting as long as the set dose is below a predefined threshold. Preventing rotation of the drive sleeve during this part of dose setting leads to retracting the drive sleeve in the proximal direction together with the dose dial sleeve which follows a helical path on the thread of the housing. As the spindle is not allowed to be retracted together with the drive sleeve, the threaded engagement between the spindle and the drive sleeve disengages such that the drive sleeve and the spindle are allowed to slide relative to each other in an axial direction. Hence, if a user attempts to administer a set dose below the threshold, the drive sleeve slides (overrides) relative to the spindle in the axial direction without dispensing medicament.

It is preferred that, when the dose dial component (e.g. a number sleeve) is rotated to select the dose less than the minimum dose, the clutch ring prevents the clutch from rotating. As the clutch is rotationally coupled to the drive sleeve, this prevents the drive sleeve from rotating as mentioned above.

On the other hand, when the dose dial component is rotated further to select a dose greater than the minimum dose, the clutch ring allows the drive sleeve and the clutch to rotate together during subsequent dose setting such that a dose greater than the minimum dose can be selected and dispensed.

There are different ways to allow the spindle and the drive sleeve to disengage during dose setting prior to setting a dose above a predefined threshold. According to a preferred embodiment of the invention, the spindle may comprise at least one flexible member, which is configured to engage a thread of the drive sleeve. In other words, the flexible member, e.g. a flexible finger, allows engagement and disengagement of the spindle and the drive sleeve. The at least one flexible member engages an inner thread of the drive sleeve after a dose has been selected that is greater than the minimum dose.

Preferably, the inner thread of the drive sleeve comprises a drive sleeve pitch wherein the drive sleeve pitch is equal to an axial distance that must be dialled by the dose dial component to reach the minimum dose. This allows the thread between the spindle and the drive sleeve to reengage after the minimum dose has been set.

The clutch ring may be splined to the housing. In more detail, it is preferred if the clutch ring is splined to the housing only when the dose dial component is rotated to select a dose that is less than the minimum dose. Further, the clutch ring is no longer splined to the housing when the dose dial component is rotated further to select a dose that is greater than the minimum dose.

The above mentioned function of the clutch ring may be achieved by providing an interface defined between a first portion of the clutch ring and a first portion of the dose dial component, which interface may define a clicker. This clicker may comprise an audible clicker. Further, the clutch and the clutch ring may comprise a unitary clutch mechanism.

As mentioned above, the clutch ring may be a separate component which may rotate relative to the clutch in a first state and which may be releasably coupled to the clutch in a second state (condition). As an alternative, the clutch ring may be formed as an integral part of the clutch or the clutch ring may be permanently coupled to the clutch. According to a further embodiment of the present invention, the clutch ring may be rotationally locked to the drive sleeve, e.g. via respective splines.

To allow decoupling of the spindle from the drive sleeve, it is preferred if the drive sleeve is axially locked to the number sleeve. Thus, the drive sleeve will move axially together with the dose dial sleeve (number sleeve) during dose dialing.

A protrusion of the clutch ring may be rotationally fixed relative to a keying feature of the housing at least when a dose is selected that is less than the minimum dose. Preferably, the housing comprises a plurality of keying features and/or wherein the clutch ring comprises a plurality of protrusions. This facilitates reengagement of the clutch ring and the housing irrespective of the angular position of the clutch ring relative to the housing.

As mentioned above, the dose setting mechanism may comprise a resettable dose setting mechanism. It is preferred to couple the dose setting mechanism to a cartridge holder containing a cartridge containing a medicament. For a resettable mechanism, the dose setting mechanism may be removably coupled to the cartridge holder.

In an exemplary min/max device, the dose count numbers (which can e.g. be printed on the dose dial component) below the minimum dose may be colored a different color such as red to differentiate that the dose dialled is less than the normal minimum dose.

These as well as other advantages of various aspects of our proposed drug delivery device will become apparent to those of ordinary skill in the art by reading the following detailed description, with appropriate reference to the accompanying drawings.

BRIEF DESCRIPTION OF THE FIGURES

Exemplary embodiments are described herein with reference to the drawings, in which:

FIG. 1B illustrates a cross-sectional view of a dose setting mechanism of the pen-type drug delivery device of FIG. 1A;

FIG. 2A illustrates a perspective view of given components of the dose setting mechanism shown in FIG. 1B;

DETAILED DESCRIPTION

Figure 1A:
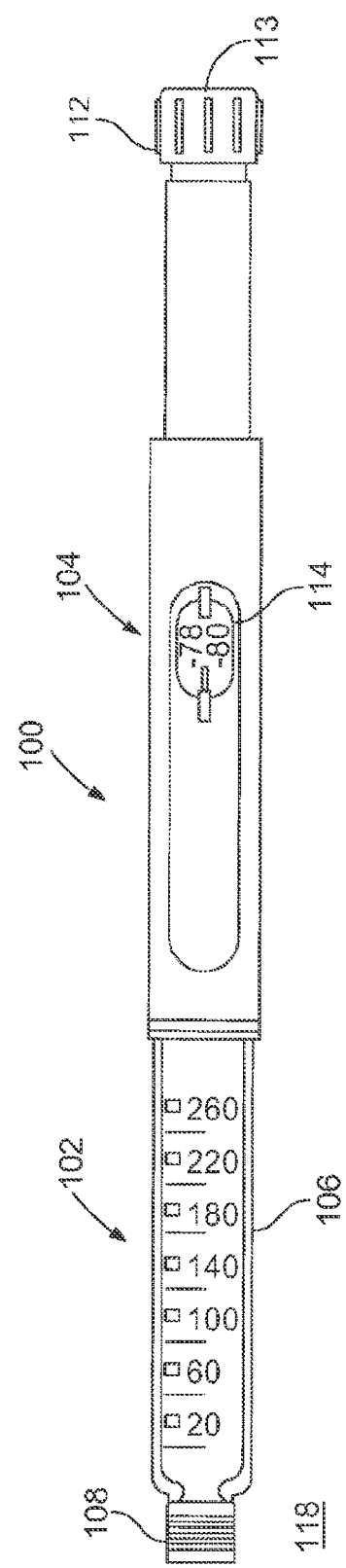
FIG. 1A illustrates an example design of a pen-type drug delivery device.

Referring to FIG. 1A, there is shown a drug delivery device 100 in accordance with an exemplary pen-type design arrangement. The drug delivery device 100 comprises a housing having a first cartridge retaining part 102, and a dose setting mechanism 104. The drug delivery device may be a resettable drug delivery device (i.e., a reusable device) or alternatively a non-resettable drug delivery device (i.e., a non-reusable device). A first end of the cartridge retaining part 102 and a second end of the dose setting mechanism 104 are secured together by connecting features. For non-resettable devices, these connecting features would be permanent and non-reversible. For resettable devices, these connecting features would be releasable.

In this illustrated arrangement, the cartridge retaining part 102 is secured within the second end of the dose setting mechanism 104. A removable cap (not shown) is releasably retained over a second end or distal end of a cartridge retaining part or cartridge housing. The dose setting mechanism 104 comprises a dose dial grip 112 and a window or lens 114. A dose scale arrangement is viewable through the window or lens 114. To set a dose of medication contained within the drug delivery device 100, a user rotates the dose dial grip 112 such that a dialled dose will become viewable in the window or lens 114 by way of the dose scale arrangement.

FIG. 1A illustrates the medical delivery device 100 with the cover cap removed from a distal end 118 of the medical delivery device 100. This removal exposes the cartridge housing 106. Preferably, a cartridge (not shown) from which a number of doses of a medicinal product may be dispensed, is provided in the cartridge housing 106. Preferably, the cartridge contains a type of medicament that can be administered relatively often, such as once or more times a day. One such medicament is either long acting or short acting insulin or an insulin analog; however, any medicament or combination of medicaments is possible. The cartridge comprises a bung or stopper that is retained near a second end or a proximal end of the cartridge. The medical delivery device also comprises a drive sleeve and a spindle (not illustrated in FIG. 1A, but is illustrated as items 124 and 126, respectively, in FIG. 1B).

The cartridge housing 106 has a distal end and a proximal end. Preferably, the distal end of the cartridge housing 106 comprises a hub 108 for attaching a removable needle assembly. However, other needle assembly connection mechanisms could also be used. If the drug delivery device 100 comprises a resettable device, the cartridge proximal end is removably connected to the dose setting mechanism 104. In one preferred embodiment, cartridge housing proximal end is removably connected to the dose setting mechanism 104 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 104 of the drug delivery device illustrated in FIG. 1A may be utilized as a reusable drug delivery device. (i.e., a drug delivery device that can be reset) Where the drug delivery device 100 comprises a reusable drug delivery device, the cartridge is removable from the cartridge housing 106. The cartridge may be removed from the device 100 without destroying the device 100 by merely having the user disconnect the dose setting mechanism 104 from the cartridge housing 106.

In use, once the cap is removed, a user can attach a suitable needle assembly to the hub 108 provided at the distal end of the cartridge housing 106. Such needle assembly may be, for example, screwed onto a distal end of the housing 106 or alternatively may be snapped onto this distal end. After use, the replaceable cap may be used to re-cover the cartridge housing 106. Preferably, the outer dimensions of the replaceable cap are similar or identical to the outer dimensions of the dose setting mechanism 104 so as to provide an impression of a unitary whole when the replaceable cap is in position covering the cartridge housing 106 when the device is not in use.

A first exemplary dose setting mechanism in accordance with our disclosure is described with reference to FIG. 1B through FIG. 3. FIG. 1B illustrates a cross-sectional view of drug delivery device 100, and in particular shows a detailed cross-sectional view of a first dose setting mechanism 104. Dose setting mechanism 104 includes a drug delivery device housing 120 and a dose dial component 122 positioned in housing 120. The dose dial component 122 is rotatable during a dosing step. In an example, the dose dial component 122 comprises a number sleeve. The dose setting mechanism 104 also includes a drive sleeve 124 positioned in the dose dial component 122 and a spindle (i.e., lead screw) 126 positioned within the drive sleeve 124. The dose setting mechanism 104 also includes a clutch 128 positioned between the dose dial component 122 and the drive sleeve 124. Further, the dose setting mechanism 104 includes a clutch ring 130. According to a first embodiment depicted in FIGS. 1B to 3, the clutch ring 130 is a separate component which is generally free to be rotated relative to the dose dial sleeve 122 and relative to the clutch 128 but which may be coupled to these components as will be explained below in detail. Further, the clutch ring 130 is generally free to be displaced axially relative to the dose dial sleeve 122 and relative to the clutch 128, at least for a limited distance.

In general, the dose setting mechanism 104 operates to ensure that a user dials a dose greater than a predetermined minimum dose before a user can administer a medicament dose. In order to ensure this, the clutch ring 130 is rotationally fixed to the housing 120 when a dose less than the minimum dose is selected. As such, when the dose dial component 122 is rotated to select a dose less than a minimum dose, the clutch ring 130 prevents the drive sleeve 124 from rotating and the spindle disengages from the drive sleeve, thereby preventing the selected dose from being administered.

Figure 2B:
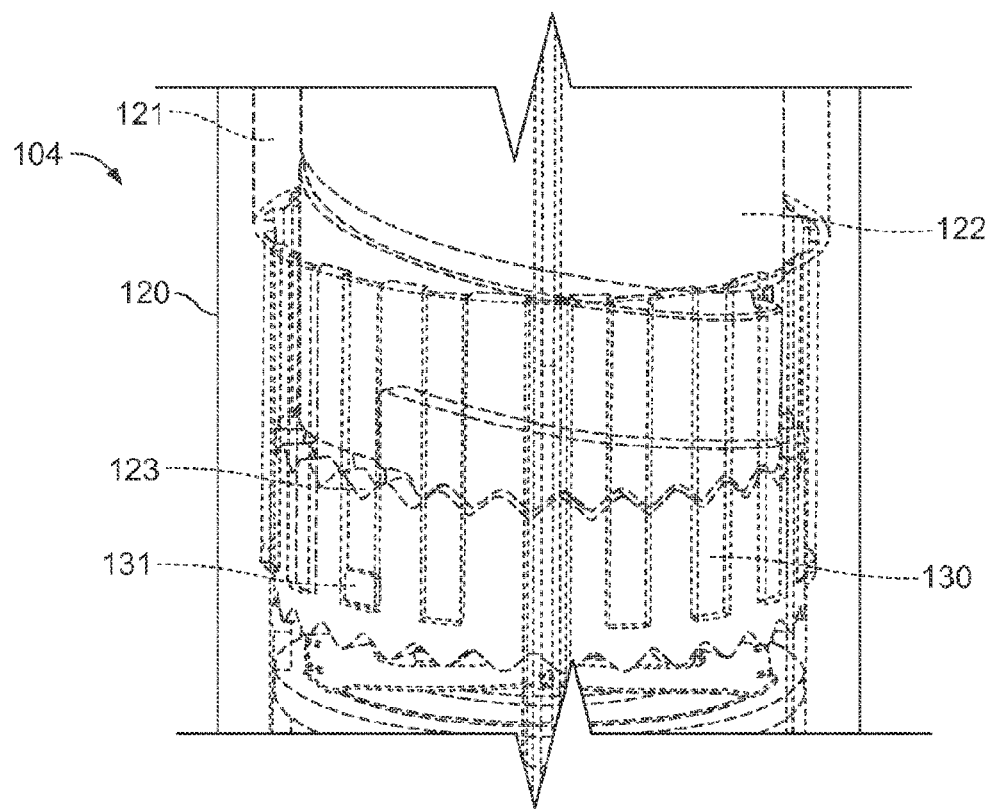
FIG. 2B illustrates a perspective view of given components of the dose setting mechanism in an initial position before a dose is dialled.

The clutch ring 130 is in engagement with the number sleeve 122, clutch 128, and a biasing element, such as metal spring 132. The clutch ring 130 may include one or more protrusions that key the clutch ring to the drug delivery device housing 120 when a dose less than the minimum dose is selected. That is, the clutch ring 130 remains keyed to the device housing 120 until a user has dialled at least a minimum dose. In one example, the clutch ring 130 is splined to the housing 120. For example, FIG. 2B illustrates a perspective view of given components of the dose setting mechanism 104 in an original or initial position before a dose is dialled. This original position is a position where the dose dial mechanism 104 has yet to dial a dose. As can be seen from FIGS. 2B and 2C, the clutch ring 130 comprises a protrusion 131 along an outer surface 133 of the clutch ring 130. Although only one protrusion is illustrated, those of skill in the art will recognize that a plurality of such protrusions may also be provided.

In addition, an inner surface 121 of the housing 120 comprises a plurality of grooves or keying features, such as keying feature 123. As illustrated in this initial position, the clutch ring protrusion 131 resides in one of the keying features 123 and resides at a most distal end of the keying feature 123.

In an alternative arrangement, the clutch ring 130 may be keyed to the housing 120 in other ways. For instance, the clutch ring 130 may be splined to a fixed member (e.g., an insert) that is attached to the housing 120.

The clutch 128 is rotationally locked to the drive sleeve 124, and the clutch 128 is capable of limited axial travel relative to the drive sleeve 124. Further, the drive sleeve 124 is axially locked to the number sleeve 122 but is not directly rotationally locked. Under certain dose dialling conditions, the clutch ring 130 may rotationally lock the clutch 128—and therefore also the drive sleeve 124—to the number sleeve 122. The metal spring 132 is keyed to the housing 120 at all times, and therefore cannot rotate.

The spindle 126 comprises at least one flexible arm, such as flexible arms 134a-b (see FIG. 1B). These flexible arms 134 a, b on the spindle 126 may be designed such that the drive sleeve 124 can travel in a proximal direction 136 without drive sleeve 124 rotating during a given length of travel. When the drive sleeve 124 travels in a proximal direction when a user initially sets a dose, this travel causes the arms 134 a, b to deflect inwards disengaging them from the drive sleeve drive internal thread 138. For example, in one arrangement, the geometry of the threaded portion of the flexible arms 134 a, b and the internal drive sleeve drive internal thread 138 includes an angled surface on one face of the threads. In such an arrangement, if the drive sleeve is moved out in a proximal direction during dose dialling (i.e., without rotation), the angled thread faces causes the spindle arms 134 a, b to deflect inwardly. Therefore the spindle 126 remains stationary as the drive sleeve 124 moves axially as the dose is dialled up from a zero dose to a minimum dose value.

The drive sleeve drive internal thread 138 pitch (i.e., the distance from one thread groove to an adjacent thread groove) may be equal to the axial distance dialled to reach the minimum dose. Therefore, once the minimum dose is dialled, the flexible arms 134 a, b may reengage with the drive sleeve drive internal thread 138. A larger dose can be dialled if required, and since the drive sleeve 124 is now free to rotate the flexible arms 134 a, b remain engaged to the drive sleeve internal thread 138. After a dose greater than or equal to the minimum dose is set, a user may deliver the dose. During dose delivery, the flexible arms have to be engaged with the drive sleeve drive internal thread 138. Thus, the drive sleeve 124 moves axially thereby causing rotation of the spindle 126 and hence transmitting the dispense force to a cartridge bung.

In accordance with various examples, the minimum dose that must be dialled may be varied from device to device. As described above, the length of the key feature along the inner surface 121 of the housing 120 that prevents rotation of the clutch ring 130 may equate to the pitch of the drive sleeve drive thread 138. Therefore, changing these values will change the minimum dose that must be dialled.

The operation of dose setting mechanism 104 is described in greater detail below with reference to the noted Figures. In FIGS. 2-3, sections of the clutch ring 130 are removed from the figures in order to show internal detail. First, the operation is described with reference to when a user dials a dose that is greater than a zero dose but less than the minimum dose of the device. The number sleeve 122 is rigidly fixed to the dial grip 112, and therefore rotating the dial grip 112 also rotates the number sleeve 122. As mentioned above, the clutch ring 130 is keyed to the housing 120 when a dose less than the minimum dose is selected and therefore below this minimum dose value, the clutch ring 130 cannot rotate.

The number sleeve 122 may include teeth 140 on the distal end of the number sleeve 122 (see FIG. 2A). Further, the clutch ring 130 may include (i) teeth 144 on the proximal end 146 of the clutch ring, (ii) teeth 148 on the distal end 150 of the clutch ring, and (iii) inner teeth 152 on an inner portion 154 of the clutch ring. When a user is dialing a dose less than the minimum dose, the distal teeth 140 of the number sleeve 122 overhaul the clutch ring upper teeth 144. This in turn causes the clutch ring 130 to oscillate axially against the metal spring 132 as the number sleeve 122 rotates. At this point, the number sleeve 122 and the clutch ring 130 interface (i.e., teeth 140 and 144) may create an audible and tactile "clicker" feedback to the user, which may provide the user with confirmation that a dose is being selected.

The outer thread 156 of the number sleeve 122 causes the number sleeve 122 to rotate and travel axially in a proximal direction as the dose is set. As this is happening, the protrusion 131 on the clutch ring 130 and the key feature 123 on the housing 120 prevent rotation of the clutch ring 130. The inner teeth 152 the clutch ring may be of a larger size than the upper teeth 144 of the clutch ring so as to help ensure that the clutch 128 and hence drive sleeve 124 do not rotate whilst the clutch ring 130 oscillates and over-rides the number sleeve teeth 140 creating the tactile "clicking" feedback. In other words, the size of the teeth 152 and the corresponding teeth on the clutch is large enough to stay engaged even if the clutch ring 130 oscillates by a distance defined by the (smaller) size of the teeth 140 overhauling teeth 144. As the dose is being set and the drive sleeve 124, the clutch 128, and the clutch ring 130 travel axially in a proximal direction 136 with the number sleeve 122, flexible arms 134 *a, b* of the spindle 126 deflect inwards as the drive sleeve 124 travels, disengaging from their drive thread 138. This allows the drive sleeve 124 to travel axially in the proximal direction without rotating whilst ensuring the spindle 126 remains stationary, thereby ensuring dose accuracy.

If the user attempted to deliver a dose when less than the minimum dose has been dialled, the drive sleeve 124 will travel axially in a distal direction 160 as a user depresses a dose button 113 of the device. However, the spindle drive arms 134 *a, b* and thus drive thread 138 will not be engaged with the drive sleeve 124. Therefore, the spindle 126 will not rotate, and consequently a dose will not be delivered. The mechanism will return to its original position as illustrated in FIG. 2B at which point the protrusion 131 returns to the most distal position of a keying feature 123 and at which point the spindle drive arms 134 *a, b* will reengage with the drive sleeve thread 138.

After the minimum user dose has been dialled, the spindle flexible arms 134 *a, b* will engage with the drive sleeve inner thread 138. In addition, at this time, the protrusion of the clutch ring 130 will exit the key features that were rotationally locking it to the housing 120. For example, FIG. 2D illustrates a perspective view of given components of the dose setting mechanism 104 immediately after a dose greater than a minimum dose has been dialled. As illustrated, the protrusion 131 has exited the keying feature 123. Therefore, as a larger dose is dialled the dual clutch ring 130 is now free to rotate with the number sleeve 122, thereby also rotating the clutch 128 and hence drive sleeve 124 and the clutch 128. During this dialling operation, the clutch ring 130 rotates and causes oscillation of the metal spring 132 as the clutch ring lower teeth 148 overhaul the metal spring 132 teeth 162. Therefore, at this stage of operation, the metal spring 132 and clutch ring 130 interface may create an audible "clicker" feedback.

After the user dials a dose greater than the minimum dose, the user may administer a dose. FIG. 3 depicts the clutch 128, clutch ring 130, number sleeve 122, and drive sleeve 124 during a dose administration step. Depressing dose button 113 acts on the clutch 128. Then, clutch 128, utilizing its limited axial travel relative to the drive sleeve 124, forces the clutch ring 130 to disengage from the number sleeve 122, as shown in FIG. 3. The metal spring 132 is compressed by the clutch ring 130, and this acts to prevent rotation of the clutch 128 and hence also acts to prevent rotation of the drive sleeve 124. As the dose is delivered, the number sleeve 122 rotates back and travels axially whilst the drive sleeve 124 and the clutch 128 travel axially without rotation, thereby forcing the spindle 126 to rotate and thus advance delivering dose delivery.

Figure 2C:
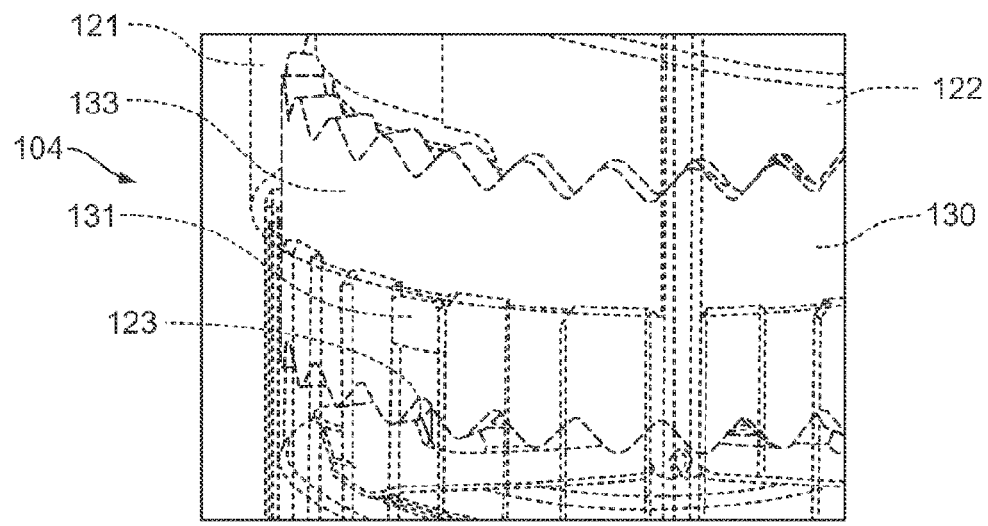
FIG. 2C illustrates a perspective view of given components of the dose setting mechanism in a certain position immediately before a dose less than a minimum dose is dialled.
Figure 2D:
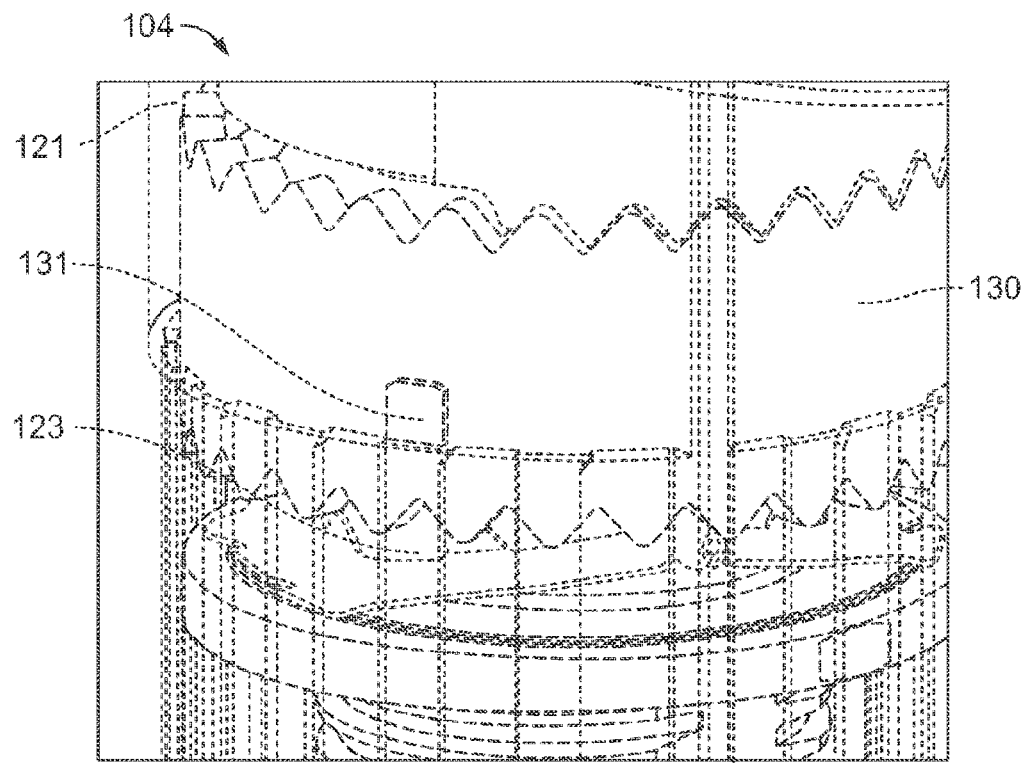
FIG. 2D illustrates a perspective view of given components of the dose setting mechanism in a certain position immediately after a dose greater than a minimum dose is dialled.
Figure 3:
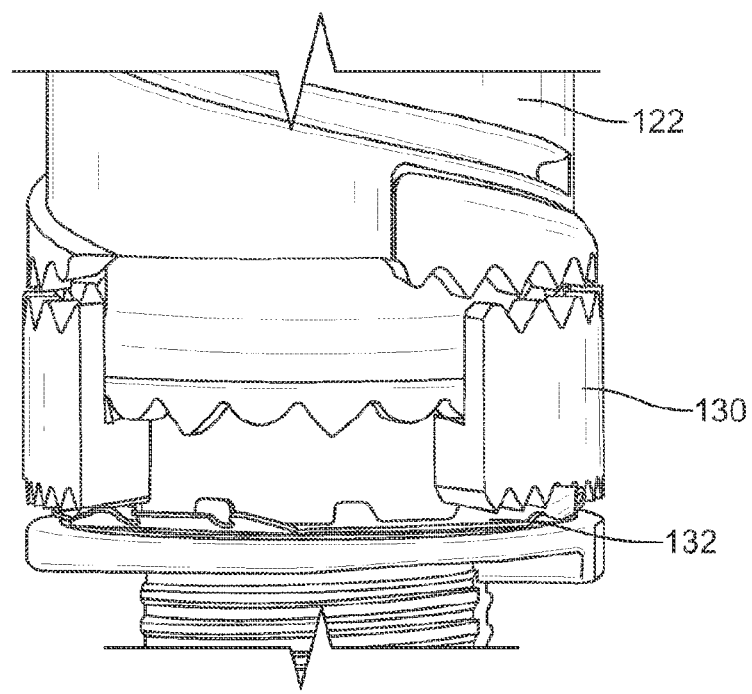
FIG. 3 illustrates a perspective view of given components of the dose setting mechanism shown in FIG. 1B.

When the clutch ring 130 returns to the axial position corresponding to the minimum dose during dose dispense, the protrusion 131 of the clutch ring 130 reengages with the keying feature 123 in the housing 120 as illustrated in FIG. 2C. This reengagement will serve to prevent rotation of the clutch ring 130 during the setting of the next dose. In an exemplary arrangement, since during dose dispense, the clutch ring 130 does not rotate but rather only moves axially in a distal direction, the clutch ring 130 may not return in the same angular orientation each time. Therefore, in an example dose setting mechanism, there may be a plurality of grooves on either clutch ring 130 or housing 122 that can engage protrusions on the other part in any of the possible rotational positions. As illustrated in FIGS. 2B-D, the internal surface 121 of this housing 120 comprises a plurality of such grooves or keying features.

In this described arrangement, clutch ring 130 and clutch 128 move together both axially and in rotation. However, the teeth features 144 and 148 of the clutch ring could be incorporated into a combined clutch/clutch ring. For instance, the clutch ring may integrated into the clutch, such that the clutch is keyed to the housing prior to a minimum dose being selected (i.e., the clutch (and hence drive sleeve) can only rotate after a minimum dose is dialled).

In an example dose setting mechanism in accordance with the present invention, the dose count numbers below the minimum dose may be coloured a different colour such as red to differentiate that the dose dialled is less than the normal minimum dose. Alternatively, the dose count numbers may not be visible until the minimum dose has been dialled.

Figure 5:
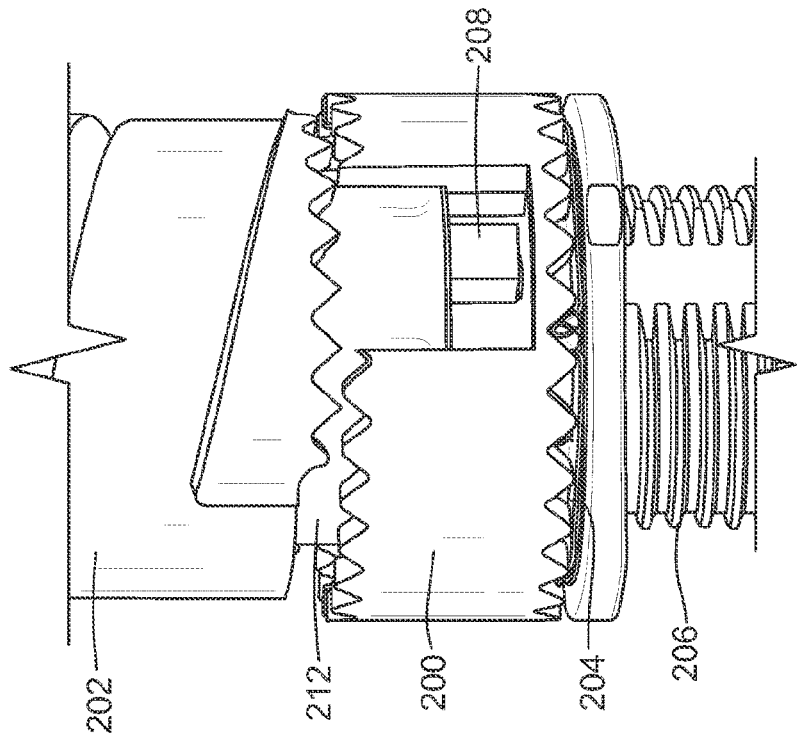
FIG. 5 illustrates a perspective view of given components of the example dose setting mechanism shown in FIG. 4.
Figure 4:
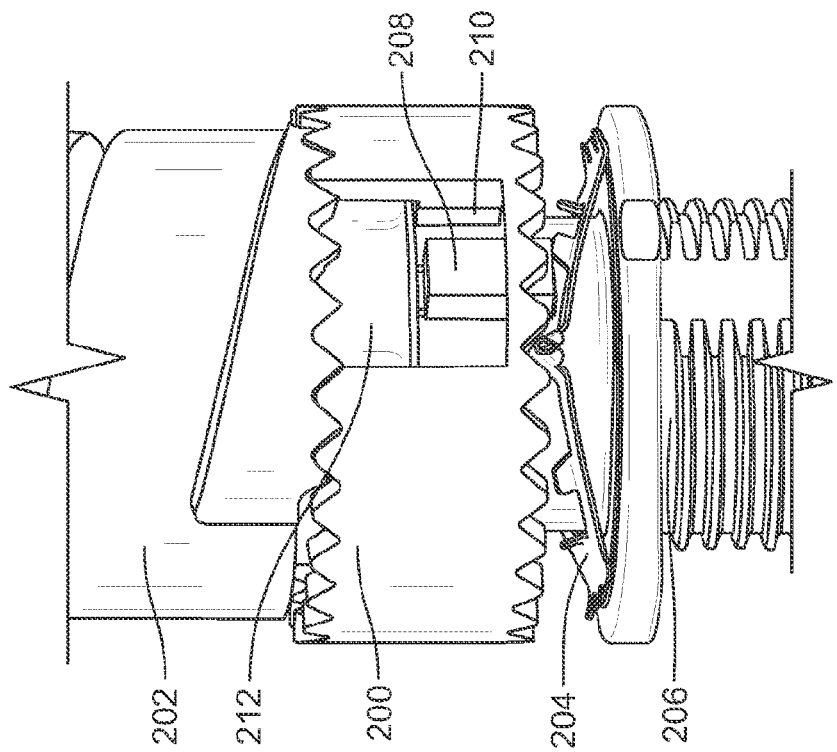
FIG. 4 illustrates a perspective view of given components of an example dose setting mechanism.

An alternative exemplary arrangement is described with reference to FIGS. 4 to 5. The dose setting mechanism of this example is similar in certain respects to the dose setting mechanism 104 shown in FIG. 1B, and thus is not described in as great level of detail. This alternative arrangement includes a modified dual clutch ring and drive sleeve. FIGS. 4 to 5 illustrates the number sleeve, clutch, clutch ring, and drive sleeve of the modified example arrangement.

In this alternative arrangement, a clutch ring 200 is provided that is in engagement with a number sleeve component 202 and a metal spring 204. The clutch ring 200 is keyed to drive sleeve 206 such that the clutch ring 200 cannot rotate, but can travel axially, relative to the drive sleeve 206. The clutch ring 200 may be keyed to the drive sleeve 206 in a variety of ways. For example, drive sleeve 206 may include at least one protrusion 208, and clutch ring 200 may include at least one corresponding protrusion 210. In FIG. 4, a section is removed from clutch ring 200 to show the internal detail of exemplary protrusions. As just one example, protrusions 208 and 210 may interact to prevent clutch ring 200 from rotating relative to the drive sleeve 206.

In one arrangement, the clutch ring is provided with a plurality of protrusions that engage a spline provided on an inner surface of the housing. As just one example, the clutch ring 200 may be provided with features such as protrusions (not shown) that key the ring 200 to the device housing until a minimum dose has been selected. Further, the drive sleeve 206 is axially locked to the dose dial component 202, but it is not directly rotationally locked to the dose dial component 202. The metal spring 204 is keyed to the device housing at all times, and hence cannot rotate.

As a user dials a dose, the clutch ring 200 is keyed to the housing and thus cannot rotate. The number sleeve 202 rotates, which causes the clutch ring 200 to oscillate axially against the metal spring 204 as the number sleeve 202 teeth over-ride the upper teeth of the dual clutch ring 200. The drive sleeve 206 travels axially in a proximal direction without rotating. As discussed above with reference to the first arrangement, the flexible arms of the spindle (not shown) operate as per the first arrangement. In this stage of operation, the "clicker" feedback may be created by the number sleeve 202 to clutch ring 200 interface. As in the first arrangement, a user is prevented from administering a dose that is less than the minimum dose due to the drive sleeve being disengaged from the spindle.

After the minimum user dose has been dialled, the spindle flexible arms reengage with the drive sleeve drive thread. The protrusion of the clutch ring 200 also exits the keying feature that were rotationally locking it to the housing as previously discussed. Therefore, as a larger dose is dialled, the clutch ring 200 is now free to rotate along with the number sleeve 202. Since the drive sleeve 206 is keyed to the clutch ring 200, the drive sleeve 206 can now rotate along with the number sleeve 202. In this stage of operation, the "clicker" feedback may be created by the metal spring 204 to dual clutch ring 200 interface.

After a dose greater than the minimum dose is set, a user may deliver the dose. To deliver a dose, a user may depress a dose button. Depressing the dose button acts on the clutch 212 disengaging the clutch ring 200 from the number sleeve 202. The metal spring 204 is compressed by the clutch ring 200 and acts to prevent rotation of the clutch ring 200 and therefore rotation of the drive sleeve 206. As the dose is delivered, the dose dial component 202 rotates and travels axially whilst the drive sleeve 206 travels axially without rotation, therefore forcing the spindle to rotate and thus advance delivering the dose.

As per the first arrangement, the dual clutch ring 200 and clutch 212 move together both axially and in rotation. In an example, the upper and lower teeth features of the dual clutch ring could be incorporated into a combined clutch/clutch ring.

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta— decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta— decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2. Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39); or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative; or an Exendin-4 derivative of the sequence H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)$_5$des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)$_5$ des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4 (1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology. Pharmaceutically acceptable solvates are for example hydrates.

TABLE 1

| Dialled Insulin Dose | Pen Number | | | |
|---|---|---|---|---|
| | 1 | 2 | 3 | 4 |
| 2 | ▨ | ▨ | ▨ | ▨ |
| 4 | ▨ | ▨ | ▨ | ▨ |
| 6 | ▨ | ▨ | ▨ | ▨ |
| 8 | ▨ | ▨ | ▨ | ▨ |
| 10 | ▨ | | ▨ | ▨ |
| 12 | ▨ | | ▨ | ▨ |
| 14 | ▨ | | ▨ | ▨ |
| 16 | ▨ | | ▨ | ▨ |
| 18 | ▨ | | ▨ | ▨ |
| 20 | ▨ | | ▨ | ▨ |
| 22 | ▨ | | ▨ | ▨ |
| 24 | ▨ | | | ▨ |
| 26 | ▨ | | | ▨ |
| 28 | ▨ | | | ▨ |
| 30 | ▨ | | | ▨ |
| 32 | ▨ | | | ▨ |
| 34 | ▨ | | | ▨ |
| 36 | ▨ | | | ▨ |
| 38 | ▨ | | | ▨ |
| 40 | ▨ | | ▨ | ▨ |
| 42 | ▨ | | ▨ | ▨ |
| 44 | ▨ | | ▨ | ▨ |
| 46 | ▨ | | ▨ | ▨ |
| 48 | ▨ | | ▨ | ▨ |
| 50 | ▨ | | ▨ | ▨ |
| 52 | ▨ | | ▨ | ▨ |
| 54 | ▨ | | ▨ | ▨ |
| 56 | ▨ | | ▨ | ▨ |
| 58 | ▨ | | ▨ | ▨ |
| 60 | ▨ | | ▨ | ▨ |
| 62 | ▨ | | ▨ | ▨ |
| 64 | ▨ | | ▨ | ▨ |
| 66 | ▨ | ▨ | ▨ | ▨ |
| 68 | ▨ | ▨ | ▨ | ▨ |
| 70 | ▨ | ▨ | ▨ | ▨ |
| 72 | ▨ | ▨ | ▨ | ▨ |
| 74 | ▨ | ▨ | ▨ | ▨ |
| 76 | ▨ | ▨ | ▨ | ▨ |
| 78 | ▨ | ▨ | ▨ | ▨ |
| 80 | ▨ | ▨ | ▨ | ▨ |

| Legend |
|---|
| ☐ Dose may be dialled and delivered |
| ▤ Low dose-Cannot be dispensed |
| ▨ High dose-Cannot be dialled |

TABLE 2

| Dialled Insulin Dose | Pen Number | | | |
|---|---|---|---|---|
| | 1 | 2 | 3 | 4 |
| 2 | | ▨ | ▨ | ▨ |
| 4 | | ▨ | ▨ | ▨ |
| 6 | | ▨ | ▨ | ▨ |
| 8 | | ▨ | ▨ | ▨ |
| 10 | | ▨ | ▨ | ▨ |
| 12 | | ▨ | ▨ | ▨ |
| 14 | | ▨ | ▨ | ▨ |
| 16 | | ▨ | ▨ | ▨ |
| 18 | | ▨ | ▨ | ▨ |
| 20 | | ▨ | ▨ | ▨ |
| 22 | | ▨ | ▨ | ▨ |
| 24 | | | ▨ | ▨ |
| 26 | | | ▨ | ▨ |
| 28 | | | ▨ | ▨ |
| 30 | | | ▨ | ▨ |
| 32 | | | ▨ | ▨ |
| 34 | | | ▨ | ▨ |
| 36 | | | ▨ | ▨ |
| 38 | | | ▨ | ▨ |
| 40 | | | ▨ | ▨ |
| 42 | | | ▨ | ▨ |
| 44 | | | ▨ | ▨ |
| 46 | | | ▨ | ▨ |
| 48 | | | ▨ | ▨ |
| 50 | | | ▨ | ▨ |
| 52 | | | ▨ | ▨ |
| 54 | | | ▨ | ▨ |
| 56 | | | ▨ | ▨ |
| 58 | | | ▨ | ▨ |
| 60 | | | ▨ | ▨ |
| 62 | | | ▨ | ▨ |
| 64 | | | ▨ | ▨ |
| 66 | | | ▨ | ▨ |
| 68 | | | ▨ | ▨ |
| 70 | | | ▨ | ▨ |
| 72 | | | ▨ | ▨ |
| 74 | | | ▨ | ▨ |
| 76 | | | ▨ | ▨ |
| 78 | | | ▨ | ▨ |
| 80 | | | ▨ | ▨ |

| Legend |
|---|
| ☐ Dose may be dialled and delivered |
| ▤ Low dose-Cannot be dispensed |
| ▨ High dose-Cannot be dialled |

TABLE 3

| Dialled Long Acting Insulin Dose | Premix Pen Number |||||| 
|---|---|---|---|---|---|---|
| | 1 | 2 | 3 | 4 | 5 | 6 |
| | Mix ratio (insulin:GLP-1) |||||| 
| | 0.83 | 0.665 | 0.53 | 0.43 | 0.35 | 0.285 |
| 2 | | | | | | |
| 4 | | | | | | |
| 6 | | | | | | |
| 8 | | | | | | |
| 10 | | | | | | |
| 12 | | | | | | |
| 14 | | | | | | |
| 16 | | | | | | |
| 18 | | | | | | |
| 20 | | | | | | |
| 22 | 18.3 | | | | | |
| 24 | 19.9 | | | | | |
| 26 | 21.6 | | | | | |
| 28 | | 18.6 | | | | |
| 30 | | 20.0 | | | | |
| 32 | | 21.3 | | | | |
| 34 | | | 18.0 | | | |
| 36 | | | 19.1 | | | |
| 38 | | | 20.1 | | | |
| 40 | | | 21.2 | | | |
| 42 | | | | 18.1 | | |
| 44 | | | | 18.9 | | |
| 46 | | | | 19.8 | | |
| 48 | | | | 20.6 | | |
| 50 | | | | 21.5 | | |
| 52 | | | | | 18.2 | |
| 54 | | | | | 18.9 | |
| 56 | | | | | 19.6 | |
| 58 | | | | | 20.3 | |
| 60 | | | | | 21.0 | |
| 62 | | | | | 21.7 | |
| 64 | | | | | | 18.2 |
| 66 | | | | | | 18.8 |
| 68 | | | | | | 19.4 |
| 70 | | | | | | 20.0 |
| 72 | | | | | | 20.5 |
| 74 | | | | | | 21.1 |
| 76 | | | | | | 21.7 |
| 78 | | | | | | |
| 80 | | | | | | |

GLP-1 Dose-may be dialled and delivered
Low dose-Cannot be dispensed
High dose-Cannot be dialled Exemplary embodiments of the present drug delivery device have been described. Those skilled in the art will understand, however, that changes and modifications may be made to these embodiments without departing from the true scope and spirit of the presently proposed dose setting mechanism for a drug delivery device, which is defined by the claims.

The invention claimed is:

1. A dose setting mechanism for a drug delivery device, the mechanism comprising:
a drug delivery device housing;
a dose dial component positioned at least partly in the housing and rotatable during a dose setting step;
a drive sleeve positioned within the dose dial component;
a spindle positioned within the drive sleeve;
a clutch positioned between the dose dial component and the drive sleeve; and
a clutch ring rotationally fixed relative to the housing when a dose less than the minimum allowable dose is selected, wherein, when the dose dial component is rotated to select a dose less than a minimum dose, the clutch ring prevents the drive sleeve from rotating, causing the spindle to be disengaged from the drive sleeve, thereby preventing the selected dose from being administered.

2. The mechanism of claim 1, wherein, when the dose dial component is rotated to select the dose less than the minimum dose, the clutch ring prevents the clutch from rotating.

3. The mechanism of claim 1, wherein, when the dose dial component is rotated to select a dose greater than the minimum dose, the clutch ring allows the drive sleeve and the clutch to rotate together during subsequent dose setting such that a dose greater than the minimum dose can be selected and dispensed.

4. The mechanism of claim 1, wherein the spindle comprises at least one flexible member, the at least one flexible member configured to engage a thread of the drive sleeve.

5. The mechanism of claim 4, wherein the at least one flexible member engages the inner thread of the drive sleeve after a dose has been selected that is greater than the minimum dose.

6. The mechanism of claim 5, wherein the drive sleeve drive inner thread comprises a drive sleeve pitch wherein the drive sleeve pitch is equal to an axial distance that must be dialed by the dose dial component to reach the minimum dose.

7. The mechanism of claim 1, wherein the clutch ring is splined to the housing.

8. The mechanism of claim 7, wherein the clutch ring is splined to the housing only when the dose dial component is rotated to select a dose that is less than the minimum dose.

9. The mechanism of claim 7, wherein the clutch ring is no longer splined to the housing when the dose dial component is rotated to select a dose that is greater than the minimum dose.

10. The mechanism of claim 1, wherein an interface defined between a first portion of the clutch ring and a first portion of the dose dial component defines a clicker.

11. The mechanism of claim 1, wherein the clutch and the clutch ring comprise a unitary clutch mechanism.

12. The mechanism of claim 1, wherein the clutch ring is rotationally locked to the drive sleeve.

13. The mechanism of claim 1, wherein the drive sleeve is axially locked to the dose dial component.

14. The mechanism of claim 1, wherein a protrusion of the clutch ring is rotationally fixed relative to a keying feature of the housing at least when a dose is selected that is less than the minimum dose.

15. The mechanism of claim 14 wherein the housing comprises a plurality of keying features and/or wherein the clutch ring comprises a plurality of protrusions.

* * * * *